(12) United States Patent
Treado et al.

(10) Patent No.: US 11,980,349 B2
(45) Date of Patent: May 14, 2024

(54) TIME CORRELATED SOURCE MODULATION FOR ENDOSCOPY

(71) Applicant: CHEMIMAGE CORPORATION, Pittsburgh, PA (US)

(72) Inventors: Patrick Treado, Pittsburgh, PA (US);
Charles Gardner, Gibsonia, PA (US);
Shona Stewart, Pittsburgh, PA (US);
Aaron Smith, Monroeville, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 0 days.

(21) Appl. No.: 16/244,845

(22) Filed: Jan. 10, 2019

(65) Prior Publication Data

US 2019/0209000 A1   Jul. 11, 2019

Related U.S. Application Data

(60) Provisional application No. 62/615,777, filed on Jan. 10, 2018.

(51) Int. Cl.
| | |
|---|---|
| *A61B 1/05* | (2006.01) |
| *A61B 1/00* | (2006.01) |
| *A61B 1/04* | (2006.01) |
| *A61B 1/06* | (2006.01) |
| *A61B 1/07* | (2006.01) |

(Continued)

(52) U.S. Cl.
CPC ............ *A61B 1/051* (2013.01); *A61B 1/0005* (2013.01); *A61B 1/00096* (2013.01); *A61B 1/00167* (2013.01); *A61B 1/046* (2022.02); *A61B 1/0607* (2013.01); *A61B 1/0638* (2013.01); *A61B 1/0646* (2013.01); *A61B 1/0676* (2013.01); *A61B 1/07* (2013.01);
*H04N 23/11* (2023.01); *H04N 23/45* (2023.01); *H04N 23/55* (2023.01); *H04N 23/56* (2023.01); *A61B 1/00009* (2013.01); *H04N 23/555* (2023.01)

(58) Field of Classification Search
CPC . A61B 1/051; A61B 1/00096; A61B 1/00167; A61B 1/0676; A61B 1/00009; H04N 5/2254
USPC ............................................. 348/76
See application file for complete search history.

(56) References Cited

U.S. PATENT DOCUMENTS

| | | | |
|---|---|---|---|
| 5,751,341 A | * | 5/1998 | Chaleki .............. A61B 1/00045 348/65 |
| 6,110,106 A | | 8/2000 | Mackinnon et al. |

(Continued)

FOREIGN PATENT DOCUMENTS

| | | |
|---|---|---|
| CN | 102215736 A | 10/2011 |
| JP | H04341232 A | 11/1992 |

(Continued)

OTHER PUBLICATIONS

International Search Report and Written Opinion for PCT/US2019/013067 dated Mar. 25, 2019.

*Primary Examiner* — Thai Q Tran
*Assistant Examiner* — Nienru Yang
(74) *Attorney, Agent, or Firm* — DLA Piper LLP (US)

(57) ABSTRACT

An endoscope has an improved chip-on-tip configuration that includes both a first configuration of source illumination fibers and a second plurality of source illumination fibers, along with a camera chip. The combination of the camera chip and the source illumination fibers on the tip of the endoscope results in endoscopes with reduced size and weight.

14 Claims, 4 Drawing Sheets

(51) Int. Cl.
*H04N 23/11* (2023.01)
*H04N 23/45* (2023.01)
*H04N 23/55* (2023.01)
*H04N 23/56* (2023.01)
*H04N 23/50* (2023.01)

(56) References Cited

U.S. PATENT DOCUMENTS

| | | | |
|---|---|---|---|
| 6,485,414 | B1 | 11/2002 | Neuberger |
| 6,663,560 | B2 | 12/2003 | MacAulay et al. |
| 9,844,334 | B2 * | 12/2017 | Stewart ................ A61B 5/4519 |
| 2004/0220478 | A1 | 11/2004 | Wallace et al. |
| 2008/0312533 | A1 * | 12/2008 | Balberg ............ A61B 5/14546 |
| | | | 600/437 |
| 2009/0076329 | A1 | 3/2009 | Su et al. |
| 2010/0262000 | A1 * | 10/2010 | Wallace ............ A61B 1/00096 |
| | | | 600/424 |
| 2013/0019930 | A1 | 1/2013 | Semonin et al. |
| 2014/0320707 | A1 * | 10/2014 | Olson .................... H04N 5/332 |
| | | | 348/262 |
| 2015/0241363 | A1 * | 8/2015 | Tuch .................. A61B 1/00009 |
| | | | 250/362 |
| 2017/0042573 | A1 * | 2/2017 | Savvouras ........ A61B 1/00154 |
| 2017/0257619 | A1 * | 9/2017 | Kashima ............ A61B 1/00188 |
| 2017/0343477 | A1 * | 11/2017 | Santori ................ G01J 3/0229 |
| 2018/0116494 | A1 | 5/2018 | Treado et al. |

FOREIGN PATENT DOCUMENTS

| | | |
|---|---|---|
| JP | H07275194 A | 10/1995 |
| JP | 2000342515 A | 12/2000 |
| JP | 2010022700 A | 2/2010 |
| JP | 2012040224 A | 3/2012 |
| JP | 2012213562 A | 11/2012 |
| JP | 2013022341 A | 2/2013 |
| WO | 9428783 A1 | 12/1994 |

\* cited by examiner

Multimode Fibers (side view)

Multimode Fibers (end-on view)

Multimode Fibers (side view)

Multimode Fibers (end-on view)

TIME CORRELATED SOURCE MODULATION FOR ENDOSCOPY

CROSS-REFERENCE TO RELATED APPLICATIONS

This application claims the priority and benefit of U.S. Provisional Application No. 62/615,777, filed Jan. 10, 2018 and entitled "TIME CORRELATED SOURCE MODULATION FOR ENDOSCOPY," the contents of which are incorporated herein by reference in its entirety.

TECHNICAL FIELD

The present disclosure relates generally to various sensor and illumination configurations for endoscopy. More specifically, the present disclosure relates to various sensor and illumination configurations for chip-on-tip endoscopy.

BACKGROUND

Endoscopes have attained great acceptance within the medical community because they allow procedures to be performed with minimal patient trauma while enabling the physician to view the internal anatomy of the patient. Depending upon the procedure, an endoscope may be inserted into a body's natural orifices or through an incision in the skin.

Conventional endoscope designs typically include an elongated tubular shaft having a rigid lens assembly or fiber optic lens assembly at one end connected to a camera or other similar light sensor via the rigid lens assembly or one or more fiber optic strands. The shaft is connected to a handle for manipulation during a procedure. Viewing is usually possible via an ocular lens in the handle and/or via an external screen. Various surgical tools may be inserted through a working channel in the endoscope for performing different surgical procedures.

However, conventional endoscope designs include various drawbacks. For example, throughput losses in acquired signals and resulting distortion of images through fiber optics connecting the camera and the lens assembly can occur during a procedure, as well as the substantial cost associated with high quality rigid lens assemblies.

Chip-on-tip endoscope configurations differ from conventional endoscope configurations in that the camera is at the tip of the endoscope rather than at the base. There are several benefits to chip-on-tip configurations. One benefit is that the camera is as close to the sample as possible, thereby reducing throughput losses for the signal and minimizing resulting distortion of images through lens assemblies and fiber optics. Another advantage to fitting the cameras on the tip of endoscopes is the potential reduction in size and weight of the endoscope system itself. Because the signal is read onto the camera chip at the tip of the endoscope, specialized optics or fiber optics are not required to relay the image to a camera at the back of the endoscope. As such, the overall number of components in the endoscope system is reduced.

SUMMARY

The disclosure is directed to various embodiments of chip-on-tip products that are used with or within an endoscope.

One embodiment provides a chip-on-tip product for use in an endoscope, the chip-on-tip product comprising a first plurality of source illumination fibers configured to transmit a first plurality of modulated photons; a second plurality of source illumination fibers configured to transmit a second plurality of modulated photons; and a first camera chip configured to detect light that includes visible (VIS), near infrared (NIR), visible-near infrared (VIS-NIR), shortwave infrared (SWIR), extended shortwave infrared (eSWIR), near infrared-extended shortwave infrared (NIR-eSWIR), and combinations thereof.

Another embodiment provides that the first camera chip is configured to detect visible light (VIS), and further comprising a second camera chip that is configured to detect visible light (VIS).

Another embodiment provides that the first camera chip is configured to detect visible light (VIS), and further comprising a second camera chip that is configured to detect near infrared light (NIR).

Another embodiment provides a color filter array provided with the first camera chip, the color filter array including BGGR, RGBG, GRGB, RGGB, RGBE, CYYM, CYGM, RGBW (2×2), RGBW (2×2 with diagonal colors), RGBW (2×2 with paired colors), RGBW (2×2 with vertical W), and 6×6 RGB in horizontal and vertical lines, and combinations thereof.

Another embodiment provides that the color filter array is selected from the group consisting of RGBW (2×2), RGBW (2×2 with diagonal colors), RGBW (2×2 with paired colors), RGBW (2×2 with vertical W), and combinations thereof; and the W tile of the color filter array is a NIR filter, a SWIR filter, or an eSWIR filter.

Another embodiment provides that the chip-on-tip product of claim 1, further comprising a third plurality of source illumination fibers configured to transmit a third plurality of unmodulated photons.

Another embodiment provides that the first chip includes silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations thereof.

One embodiment provides an endoscope system, the endoscope system comprising a chip-on-tip product that includes a first plurality of source illumination fibers configured to transmit a first plurality of modulated photons; a second plurality of source illumination fibers configured to transmit a second plurality of modulated photons; and a first camera chip configured to detect light that includes visible (VIS), near infrared (NIR), visible-near infrared (VIS-NIR), shortwave infrared (SWIR), extended shortwave infrared (eSWIR), near infrared-extended shortwave infrared (NIR-eSWIR), and combinations of any of the above; a light source; a first modulator that modulates at least the first plurality of modulated photons for the first plurality of source illumination fibers; and a second modulator that modulates at least the second plurality of modulated photons for the second plurality of source illumination fibers.

Another embodiment provides that the first camera chip is configured to detect visible light (VIS), and wherein the chip-on-tip product further includes a second camera chip that is configured to detect visible light (VIS).

Another embodiment provides that the first camera chip is configured to visible light (VIS), and wherein the chip-on-tip product further includes a second camera chip that is configured to detect near infrared light (NIR).

Another embodiment provides that the chip-on-tip product further includes a color filter array provided with the first camera chip, the color filter array including BGGR, RGBG, GRGB, RGGB, RGBE, CYYM, CYGM, RGBW (2×2), RGBW (2×2 with diagonal colors), RGBW (2×2 with paired colors), RGBW (2×2 with vertical W), and 6×6 RGB in horizontal and vertical lines, and combinations thereof.

Another embodiment provides that the color filter array is selected from the group consisting of RGBW (2×2), RGBW (2×2 with diagonal colors), RGBW (2×2 with paired colors), RGBW (2×2 with vertical W), and combinations thereof; and the W tile of the color filter array is a NIR filter, a SWIR filter, or an eSWIR filter.

Another embodiment provides that the chip-on-tip product further includes a third plurality of source illumination fibers configured to transmit a third plurality of unmodulated photons.

Another embodiment provides that the light source includes an incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, or combinations thereof.

Another embodiment provides that the first camera chip includes silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations thereof.

Another embodiment provides that the chip-on-tip product further includes a second camera chip, and the first camera chip and second camera chip are configured to generate a stereoscopic image.

In one embodiment, there is a method of generating a fused image using an endoscope system, the method comprising providing the endoscope system of claim 8; generating a first image from a first plurality of modulated photons; generating a second image from a second plurality of modulated photons; and overlaying the first image and the second image to thereby generate a fused image.

Another embodiment further provides generating a third image from a third plurality of unmodulated photons.

Another embodiment provides that the third plurality of unmodulated photons are NIR photons, SWIR photons, eSWIR photons, or combinations thereof.

Another embodiment provides that the first plurality of modulated photons and the second plurality of modulated photons are VIS or VIS-NIR.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
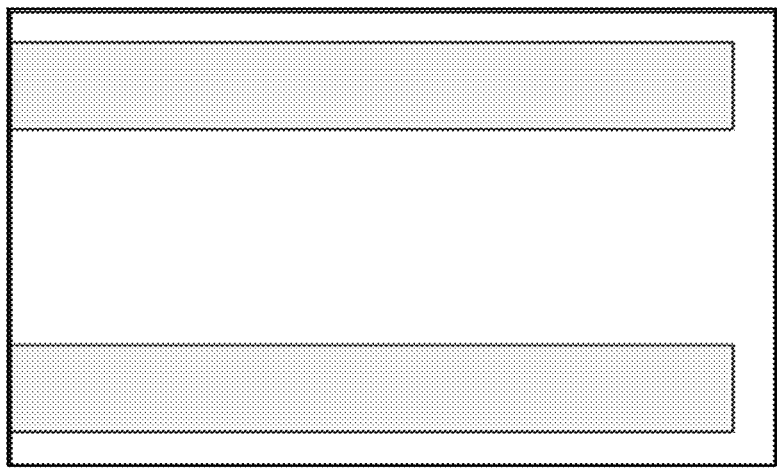
FIG. 1 illustrates a first variation of an endoscope in accordance with the present disclosure.
Figure 1:
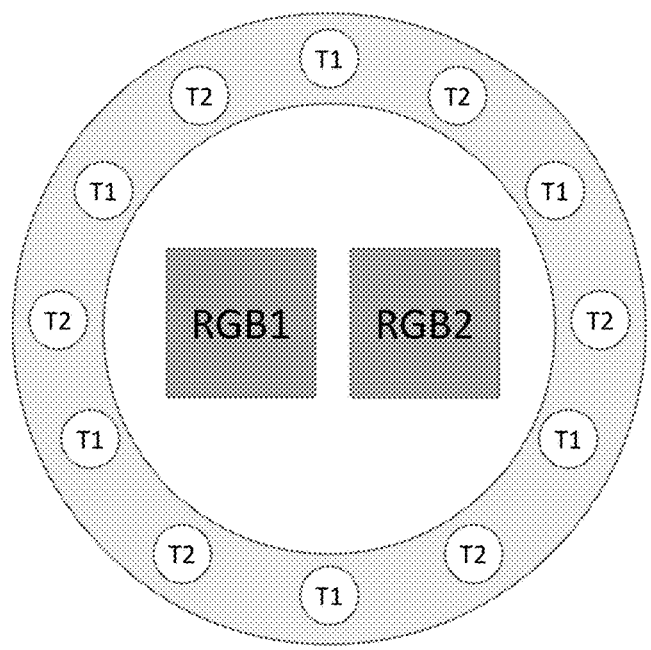

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

As noted above, conventional endoscopes include a fiber optic lens assembly at one end connected to a camera or other similar light sensor via one or more fiber optic strands. In order to acquire multispectral data from a conventional endoscope imaging system, the signal acquired from a sample is tuned selectively, often by one or more in-line filters, before reaching the camera. In endoscope systems with the camera (or chip) on the tip of the endoscope, it is not readily possible without significant miniaturization of filtering technology to filter the sample image. Instead, the source illumination is filtered before reaching the sample. The sample signal is then read by the camera at the tip of the endoscope.

This disclosure describes three chip-on-tip endoscope imaging variations. These variations include filtering the source illumination prior to sample imaging. In each of the variants, source filtering and/or modulation can be performed by, for example, an optical imaging filter such as an acousto-optic tunable filter (AOTF), a liquid crystal tunable filter (LCTF), and a sequential scan tunable filter including, for example, a multi-conjugate filter (MCF) or conformal filter (CF). It should be noted, however, that MCFs and CFs are described herein by way of examples only. Additional filters such as multivariate optical elements (MOEs), MOE filter and filter wheel arrangements, patterned etalon filters, and other similar filters can be used to filter the source illumination. Additional examples of source illumination processing and filtering can be found in U.S. patent application Ser. No. 15/374,769 which is published as U.S. Patent Application Publication No. 2018/0116494, the content of which is incorporated herein by reference in its entirety. The above source filtering and/or modulation is denoted in some embodiments of the specification as being performed by a "modulator," which refers to any of the devices that modulate the photons from the light source.

As described herein, the three variations comprise the camera chips placed in the center of the endoscope tip and surrounded by the source illumination fibers. However, it should be noted that this central arrangement is provided by way of example only, and additional arrangements of the camera chips and the source illumination fibers can be included.

The endoscope variations as described herein can include various illumination sources. In certain implementations, a single light source can be used in combination with various configurations of beamsplitters and/or mirrors to provide multiple light beams. These multiple light beams can then be directed to the endoscope tip using, for example, different source illumination fibers or sets of source illumination fibers. For example, in the variation shown in FIG. 1, a single light source can be split into two separate beams and directed to two sets of source illumination fibers. In other implementations, such as the options illustrated in FIG. 4, a single light source can be split into separate beams, or redirected via one or more mirrors, to provide source illumination for three sets of source illumination fibers. It should be noted that although only a single light source is shown, for example, in FIGS. 1 and 4, the disclosure is not limited to a single light source. It is contemplated that additional light sources can be included in one or more of the endoscope variations as described herein. Such endoscope variations can include a plurality of separate and distinct light sources used alone or in combination.

The light source is not limited and can be any source that is useful in providing the necessary illumination for the endoscope other ancillary requirements, such as power consumption, emitted spectra, packaging, thermal output, and so forth. In some embodiments, the light source is an incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, or any combination of these light sources. In some embodiments, the light source is a tunable light source, which means that the light source is monochromatic and can be selected to be within any desired wavelength range. The selected wavelength of the tunable light source is not limited and can be any passband within the ultraviolet (UV), visible (VIS), near infrared (NIR), visible-near infrared (VIS-NIR), shortwave infrared (SWIR), extended shortwave infrared (eSWIR), and near infrared-extended shortwave infrared (NIR-eSWIR) ranges. The wavelength ranges are described below.

The disclosed variations of the endoscopes include at least one camera chip which is used as an image sensor to detect incoming photons and output that information to form an image. The functionality and construction of the camera chip is not limited. In some embodiments, the camera chip is characterized by the wavelengths of light that it is capable of imaging. The wavelengths of light that can be imaged by the camera chip are not limited, and include ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR). These correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), and about 720 nm to about 2500 nm (NIR-eSWIR). The above ranges may be used alone or in combination of any of the listed ranges. Such combinations include adjacent (contiguous) ranges, overlapping ranges, and ranges that do not overlap. The combination of ranges may be achieved by the inclusion of multiple camera chips, each sensitive to a particular range, or a single camera chip that by the inclusion of a color filter array can sense multiple different ranges.

In some embodiments, the camera chip is characterized by the materials from which it is made. The materials of the camera chip are not limited and can be selected based on the wavelength ranges that the camera chip is expected to detect. In such embodiments, the camera chip is based on silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations of any of these.

In some embodiments, the camera chip is characterized by its electrical structure. The electrical structure is not limited the camera chip includes a charge coupled device (CCD) or a complementary metal oxide semiconductor (CMOS) image sensor. It should be noted that the materials listed above can each be used with either electrical structure to form the final camera chip. Examples include Si CMOS, Si CCD, Ge CCD, Ge CMOS, InGaAs CCD, InGaAs CMOS, PtSi CCD, PtSi CMOS, HgCdTe CCD, HgCdTe CMOS, InSb CCD, InSb CMOS, CQD CCD, or CQD CMOS. These sensor structures may be used alone or in combination, either in the same physical camera chip or in multiple separate camera chips.

In some embodiments, the camera chip is provided with a color filter array to produce images. The design of the filter array is not limited. It is to be understood that the term "filter" when used in the context of a camera chip means that the referenced light is allowed to pass through the filter. For example, a "green filter" is a filter that appears green to the human eye by only allowing light having a wavelength of about 520 nm to about 560 nm to pass through the filter, corresponding to the visible color green. A similar "NIR filter" only permits near infrared light (NIR) to pass through. In some embodiments, the filter is a color filter array that is positioned over a camera chip. Such color filter arrays are varied in design but are all related to the original "Bayer" filter color mosaic filters. The color filter array includes BGGR, RGBG, GRGB, RGGB, RGBE, CYYM, CYGM, RGBW (2×2), RGBW (2×2 with diagonal colors), RGBW (2×2 with paired colors), RGBW (2×2 with vertical W), and X-TRANS (sold by Fujifilm Corporation of Tokyo, Japan). The X-TRANS sensor has a large 6×6 pixel pattern that reduces Moiré effect artifacts by including RGB tiles in all horizontal and vertical lines. In the listings, B corresponds to blue, G to green, R to red, E to emerald, C to cyan, Y to yellow, and M to magenta. W corresponds to a "white" or a monochrome tile, which will be further described below.

The W or "white" tile itself includes several configurations. In some embodiments, the W tile does not filter any light, and so all light reaches the camera chip. In those embodiments, the camera chip will detect all of the light that it is capable of detecting. Depending on the camera chip, this can be UV, VIS, NIR, VIS-NIR, VIS-NIR, VIS-SWIR, or VIS-eSWIR. In some embodiments, the W tile is a filter for VIS, VIS-NIR, NIR, or eSWIR, allowing only VIS, VIS-NIR, NIR, or eSWIR respectively to reach the camera chip. This may be advantageously combined with any of the camera chips materials or electrical structures listed above. Such a filter array can be useful because it enables a single camera chip to detect both visible light and near infrared light, and are sometimes referred to as a four-band filter array.

In still further embodiments, the color filter array is omitted and is not provided with the camera chip, which produces a monochromatic image. In such embodiments, the generated image is based solely on the band gap of the materials that make up the camera chip. In other embodiments, a filter is still applied to the camera chip, but only as a monolithic, single filter. For example, the application of a red filter means that the camera chip generates monochromatic images representative of red spectrum. In some embodiments, multiple camera chips, each with a different monolithic, single filter camera chip are employed. As an example, a VIS image can be produced by combining three camera chips, each having R, G, and B filters respectively.

In another example, a VIS-NIR image can be produced by combining four camera chips, each having R, G, B, and NIR filters respectively. In another example, a VIS-eSWIR image can be produced by combining four camera chips, each having R, G, B, and eSWIR filters respectively.

In some embodiments, the color array is omitted and the camera chip utilizes vertically stacked photodiodes organized in to a pixel grid. Each of the stacked photodiodes responds to the desired wavelengths of light. For example, a stacked photodiode camera chip includes R, G, and B layers to form a VIS image. In another embodiment, the stacked photodiode camera chip includes R, G, B, and NIR layers to form a VIS-NIR image. In another embodiment, the stacked photodiode camera chip includes R, G, B, and eSWIR layers to form a VIS-eSWIR image.

In those embodiments where two or more camera chips included, a stereoscopic image may be generated based on the images from each of the two or more camera chips. Stereoscopic images are useful because they permit a viewer to perceive depth in the image, which increases accuracy and realism of the perception. During surgery or other similar endoscopic activities, this is useful for manipulating instruments and performing tasks, with greater safety and accuracy than with monoscopic endoscopes. This is because monoscopic endoscopes, having only one camera chip position, cannot provide depth perception. In some embodiments, the stereoscopic image is formed by using two camera chips and two color filter arrays that are the same. In some embodiments, the stereoscopic image is formed by two camera chips that are the same, but each provided with a different color filter array. In some embodiments, the stereoscopic image is formed by two camera chips that are different, provided with two color filter arrays that are different. In some embodiments, the stereoscopic image is formed by two camera chips that are different, with only one camera chip being provided a color filter array, and the other camera chip being provided either a monochromatic filter or no filter array at all. Anytime that there is more than one camera chip provided, a stereoscopic image can be generated by using the output of each camera chip and combining or fusing the output of each camera chip.

In still further embodiments, methods of obtaining stereoscopic images are provided. For example, a first camera chip generates a first image, a second camera chip at a different position generates a second image, and the first image and the second image are combined ("fused") to form a stereoscopic image.

FIG. 1 illustrates a first endoscope variation in accordance with the present disclosure. As shown in FIG. 1, an endoscope can be equipped with two red-green-blue (RGB) cameras RGB1 and RGB2 in the tip, surrounded by two sets of source illumination fibers T1 and T2. As shown in the end-on view in FIG. 1, the source illumination fibers T1, T2 can be arranged in an alternating manner around the circumference of the endoscope. Such an arrangement can provide for more uniform and consistent lighting around the circumference of the endoscope. However, it should be noted that the alternating arrangement is provided by way of example only, and additional arrangements of the source illumination fibers can be included in the design.

In some implementations, the source illumination fibers T1 and T2 can represent two discrete wavelengths filtered through sequential scan MCFs or a plurality of wavelengths filtered through CFs. For example, T1 and T2 can be modulated selectively or delivered to the sample simultaneously. As shown in the circuit diagram included in FIG. 1, a single light source can be directed at a beamsplitter. The beamsplitter can be configured to split the light received from the light source into two beams. A first beam can be directed down a T1 source illumination path to a modulator and filter (e.g., an MCF and/or a CF). Similarly, a second beam can be directed down a T2 source illumination path to a second modulator and filter (e.g., an MCF and/or a CF). By actively controlling the operation of the modulators and configuration of the filters, either or both of the first and second plurality of source illumination fibers T1 or T2 can illuminate a tissue sample at their respective discrete wavelengths.

In some implementations, the two cameras RGB1 and RGB2 can be configured to perform separate imaging functions. For example, RGB1 can be tuned and configured to provide sample images when the sample tissue is illuminated using source illumination fibers T1. Conversely, RGB2 can be tuned and configured to provide sample images when the sample tissue is illuminated using source illumination fibers T2. In other implementations, RGB1 may be implemented as a low-resolution camera, and RGB2 may be implemented as a high-resolution camera. In such an example, both cameras may be configured to capture images using either source illumination fibers T1 and T2.

Figure 2:
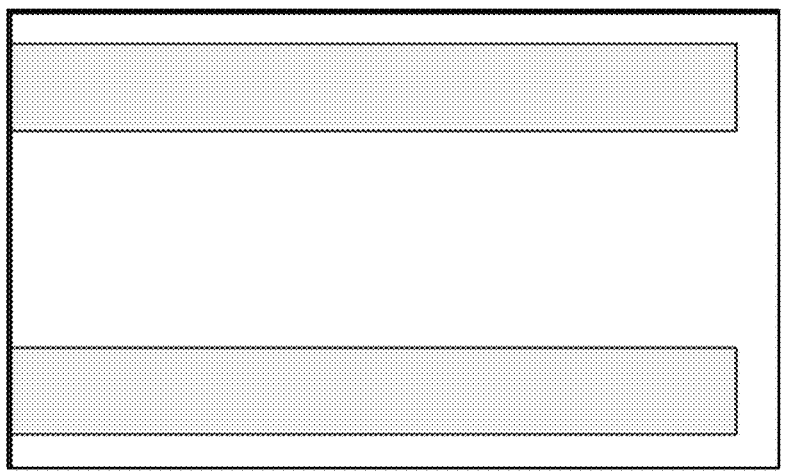
FIG. 2 illustrates a second variation of an endoscope in accordance with the present disclosure.
Figure 2:
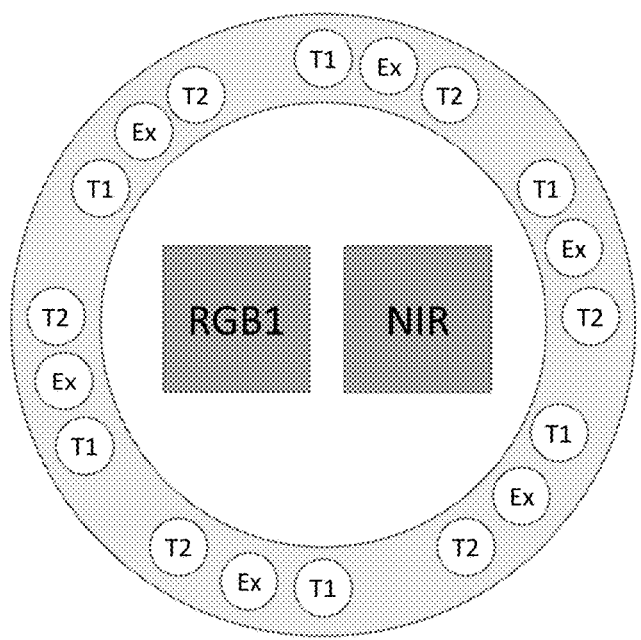

FIG. 2 illustrates a second endoscope variation in accordance with the present disclosure. As shown in FIG. 2, an endoscope can be equipped with one RGB camera and one near infrared (NIR) camera. Several fibers including source illumination fibers T1 and T2 (similar to T1 and T2 as described above), and a third source illumination fiber, Ex, can be arranged such that they surround the two camera chips. As described herein, source illumination fiber Ex can be configured to direct light which has an excitation wavelength for NIR fluorescence imaging. In some implementations, the illumination fibers can be arranged in multiple groups of three. For example, as shown in the end-on view in FIG. 2, the groups of three can alternate between T1, Ex, and T2. However, it should be noted that the alternating arrangement shown in FIG. 2 is provided by way of example only. Alternate and/or additional arrangements of the source illumination fibers can be used in the design.

Similar to the above discussion of FIG. 1, T1 and T2 can represent two discrete wavelengths filtered through sequential scan MCFs or a plurality of wavelengths filtered through CFs. In some implementations, all three illumination sources T1, T2, and Ex can be presented simultaneously to the sample. In some examples, illumination sources T1 and T2 can be delivered independently from illumination source Ex.

In some implementations, an image of a tissue sample illuminated using the T1 and T2 illumination source fibers can be recorded using the RGB camera. In such an arrangement, a fluorescence image of the tissue sample illuminated using the Ex source illumination fibers can be recorded using the NIR camera. However, it should be noted that such an arrangement is provided by way of example only, and the functionality of the cameras can be altered based upon the modulation, filtering, and other similar factors related to the source illumination fibers.

Figure 3:
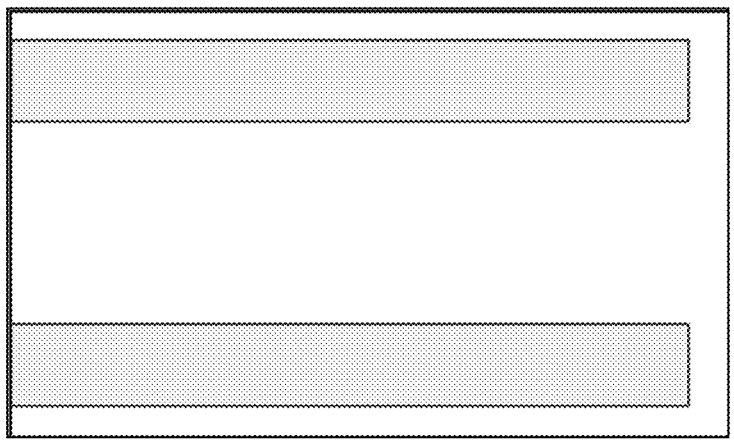
FIG. 3 illustrates a third variation of an endoscope in accordance with the present disclosure.
Figure 3:
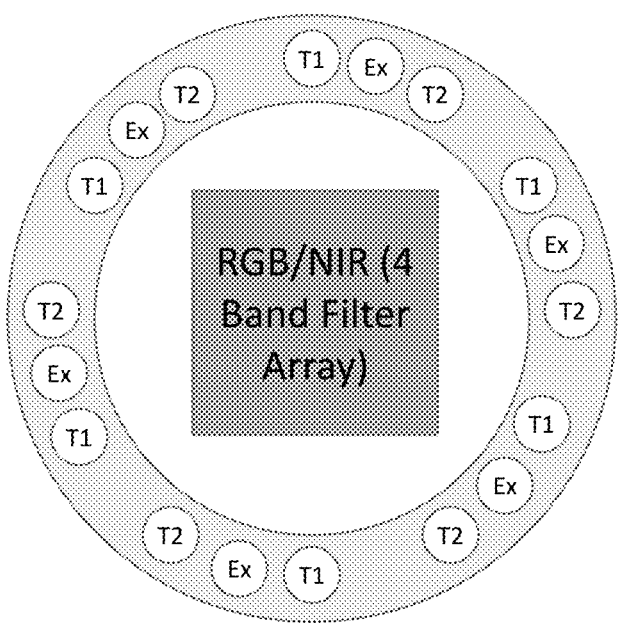

FIG. 3 illustrates a third endoscope variation in accordance with the present disclosure. As shown in FIG. 3, an endoscope can be equipped with a four-band filter array comprising red, green, blue, and NIR filters over the camera chip. Similar to the arrangement as described above in regard to FIG. 2, several fibers including source illumination fibers T1 and T2, and a third source illumination fiber, Ex, may surround the camera chip(s). In some implementations, the illumination fibers can be arranged in multiple groups of three. For example, as shown in the end-on view in FIG. 3, the groups of three can alternate between T1, Ex, and T2. However, it should be noted that the alternating arrangement shown in FIG. 3 is provided by way of example only. Alternate and/or additional arrangements of the source illumination fibers can be used in the design.

Similar to the above discussion of FIG. 1, T1 and T2 can represent two discrete wavelengths filtered through sequential scan MCFs or a plurality of wavelengths filtered through CFs. In some implementations, all three illumination sources T1, T2, and Ex can be presented simultaneously to the sample. In some examples, illumination sources T1 and T2 can be delivered independently from illumination source Ex.

In some implementations, tissue samples imaged using T1 and T2 illumination source fibers can be recorded using the red, green, and/or blue filtered pixels of the filter array. In such an arrangement, fluorescence images generated using the Ex source illumination fibers can be recorded using the NIR filtered pixels.

Figure 4:
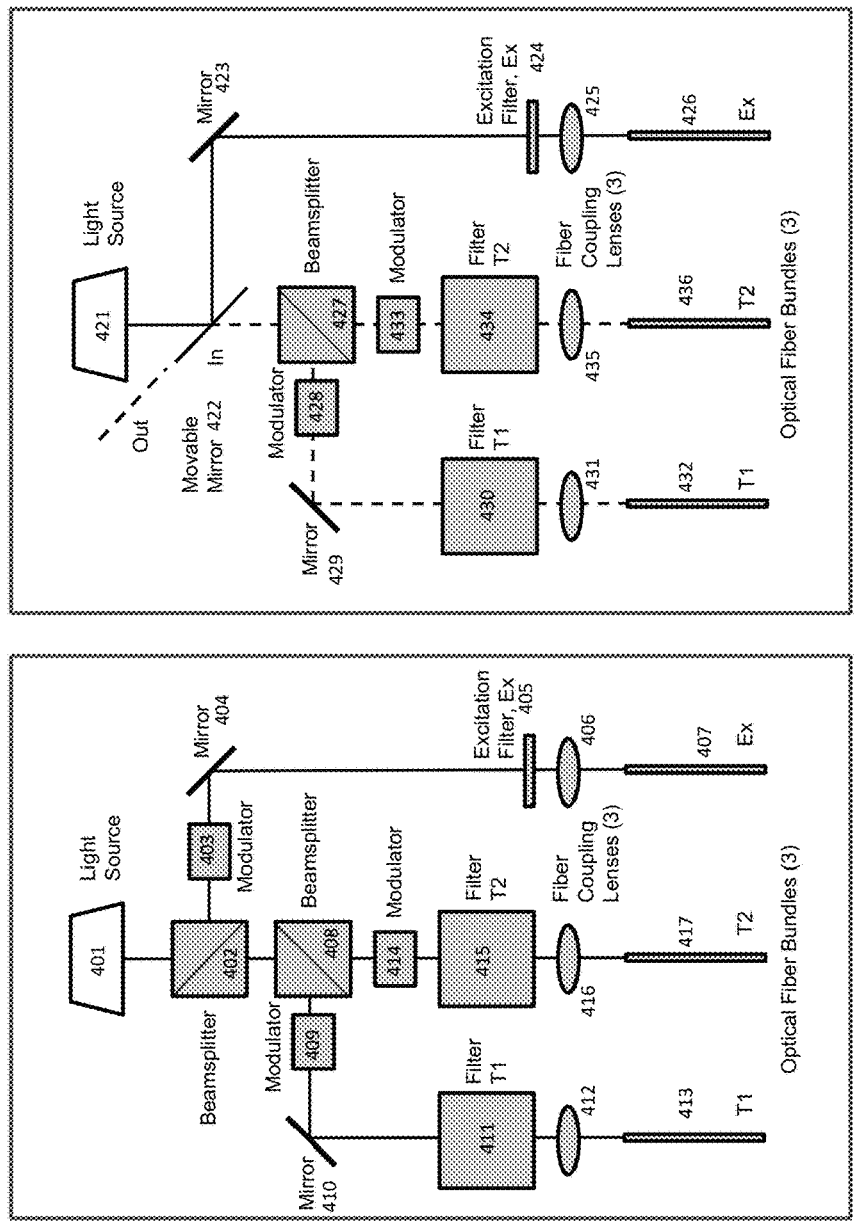
FIG. 4 illustrates two optical configuration options for use with one of the endoscope variations as shown in FIGS. 1-3 in accordance with the present disclosure.

The three variations as described in reference to FIGS. 1-3 above can be implemented using one of the two optical configuration options shown in FIG. 4. A first optical configuration, labeled Option 1 in FIG. 4, includes a light source 401 directed at a beamsplitter 402. The beamsplitter 402 can be configured to split the beam into two beams such that each of the split beams includes about 50% of the original light emitted by the light source 401, a first split light beam being directed through the Ex source illumination path and a second split light beam directed through the T1 and T2 source illumination path. Following the Ex source illumination path, the first split light beam can be directed through a modulator 403, and reflected by a mirror 404 to an excitation filter 405. The output of the excitation filter 405 can pass through a fiber coupling lens 406 and be output through the Ex source illumination optical fiber bundle 407. Following the T1 and T2 path, the second split light beam can pass through a second beamsplitter 408. The output of the second beamsplitter 408 can be two equal beams, now each approximately 25% of the total light emitted by the light source 401. The first beam can pass through a modulator 409, be reflected by a mirror 410, and filtered by a filter 411. The filtered beam can pass through a fiber coupling lens 412 and be output through the T1 source illumination optical fiber bundle 413. The second beam (from beamsplitter 408) can pass through a modulator 414 and be filtered by a filter 415. The filtered beam can pass through a fiber coupling lens 416 and be output through the T2 source illumination optical fiber bundle 417.

By actively controlling the operation of one or more of the modulators 403, 409, and 414, the output of the configuration as shown in Option 1 can be accurately controlled. For example, by activating modulators 409 and 414, and deactivating modulator 403, both T1 and T2 can actively output source illumination. Similarly, by activating modulator 403 and deactivating modulators 409 and 414, Ex can actively output source illumination.

A second optical configuration, labeled Option 2 in FIG. 4, includes a light source 421 directed at a movable mirror 422. Depending upon the position of the movable mirror 422, the light emitted from the light source 421 can either travel the Ex source illumination path (represented by the solid line in Option 2) or travel the T1 and T2 source illumination path (represented by the dashed line in Option 2).

Following the Ex source illumination path, the light reflected by the movable mirror 422 can be further reflected by a mirror 423 to an excitation filter 424. The output of the excitation filter 424 can pass through a fiber coupling lens 425 and be output through the Ex source illumination optical fiber bundle 426.

If the movable mirror 422 is positioned such that the light emitted by the light source 421 is not reflected, the light can follow the T1 and T2 path. The light beam can pass through a beamsplitter 427. The output of the beamsplitter 427 can be two equal beams, now each approximately 50% of the total light emitted by the light source 421. The first beam (from beamsplitter 427) can pass through a modulator 428, be reflected by a mirror 429, and be filtered by a filter 430. The filtered beam can pass through a fiber coupling lens 431 and be output through the T1 source illumination optical fiber bundle 432. The second beam (from beamsplitter 427) can pass through a modulator 433 and be filtered by a filter 434. The filtered beam can pass through a fiber coupling lens 435 and be output through the T2 source illumination optical fiber bundle 436.

By actively controlling the position of the movable mirror 422, as well as the operation of one or more of the modulators 428 and 433, the output of the configuration as shown in Option 2 can be accurately controlled. For example, by moving movable mirror 422 into position to reflect the light emitted by light source 421, all emitted light can be directed to the Ex optical fiber bundle 426. Similarly, by positioning the movable mirror 422 into a position where no light emitted by the light source 421 is reflected, and by actively controlling modulators 428 and 433, light can be output to one or more of the T1 source illumination optical fiber bundle 432 and the T2 source illumination optical fiber bundle 436.

The table in FIG. 4 compares the relative illumination intensity throughput and other performance metrics of configuration Options 1 and 2. However, it should be noted that the specific values contained in the table are relevant to the particular designs included in Options 1 and 2, which are provided by way of example only. Depending upon the design of and implementation of an endoscopy system, the designs shown in Options 1 and 2 can be modified accordingly. For example, depending upon the available space for circuit implementation, the number of and/or position of the mirrors in the configurations may be altered. Additionally, in certain implementations, the function of the movable mirror 422 of Option 2 may be altered. For example, when in a position to reflect light, the movable mirror 422 may be configured to direct the reflected light to the T1 and T2 pathway while non-reflected light (i.e., the movable mirror 422 is in a position where light emitted from the light source 421 is not reflected) travels down the Ex pathway.

In some embodiments, the chip-on-tip product or the endoscope system of is used as part of a method of generating an fused image. In such embodiments, a first plurality of modulated photons are used to generate a first image, and a second plurality of modulated photons are used to generate a second image. The first image and the second image are used to generate a fused image. In some embodiments, additional images beyond the first image and the second image are generated, and the additional images may be generated from modulated and/or unmodulated photons. Each of the first, second and additional images may be generated from photons in the ranges of ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR). In some embodiments, the plurality of unmodulated photons are NIR, SWIR, or eSWIR photons. In other embodiments, a first plurality of modulated photons are VIS and a second plurality of modulated photons are VIS-NIR.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An endoscope system for illuminating a sample, the endoscope system comprising:
a distal end;
a chip-on-tip product that includes:
a first plurality of source illumination fibers configured to transmit a first plurality of modulated photons at the sample, the first plurality of modulated photons having a first wavelength;
a second plurality of source illumination fibers configured to transmit a second plurality of modulated photons at the sample, the second plurality of modulated photons having a second wavelength that is different from the first wavelength; and
a first camera chip configured to detect light that includes visible (VIS), near infrared (NIR), visible-near infrared (VIS-NIR), shortwave infrared (SWIR), extended shortwave infrared (eSWIR), near infrared-extended shortwave infrared (NIR-eSWIR), and combinations of any of the above;
wherein the first plurality of source illumination fibers, the second plurality of source illumination fibers, and the first camera chip are positioned at the distal end;
a light source;
a first modulator optically coupled to the light source and the first plurality of source illumination fibers, the first modulator configured to modulate light from the light source to generate the first plurality of modulated photons for the first plurality of source illumination fibers; and
a second modulator optically coupled to the light source and the first plurality of source illumination fibers, the second modulator configured to modulate the light from the light source to generate the second plurality of modulated photons for the second plurality of source illumination fibers;
wherein the first modulator and the second modulator are selectively activatable to cause the sample to be exposed to the first plurality of modulated photons, the second plurality of modulated photons, or a combination thereof, and the chip-on-tip product further includes a second camera chip positioned at the distal end, and the first camera chip and second camera chip are configured to generate a stereoscopic image, and wherein the first modulator is a conformal filter.

2. The endoscope system of claim 1, wherein the first camera chip is configured to detect visible light (VIS), and wherein the chip-on-tip product further includes a second camera chip that is configured to detect visible light (VIS).

3. The endoscope system of claim 1, wherein the first camera chip is configured to visible light (VIS), and wherein the chip-on-tip product further includes a second camera chip that is configured to detect near infrared light (NIR).

4. The endoscope system of claim 1, wherein the chip-on-tip product further includes a color filter array provided with the first camera chip, the color filter array including BGGR, RGBG, GRGB, RGGB, RGBE, CYYM, CYGM, RGBW (2×2), RGBW (2×2 with diagonal colors), RGBW (2×2 with paired colors), RGBW (2×2 with vertical W), and 6×6 RGB in horizontal and vertical lines, and combinations thereof.

5. The endoscope system of claim 4, wherein:
the color filter array is selected from the group consisting of RGBW (2×2), RGBW (2×2 with diagonal colors), RGBW (2×2 with paired colors), RGBW (2×2 with vertical W), and combinations thereof; and
the W tile of the color filter array is a NIR filter, a SWIR filter, or an eSWIR filter.

6. The endoscope of claim 1, wherein the chip-on-tip product further includes a third plurality of source illumination fibers configured to transmit a third plurality of unmodulated photons.

7. The endoscope of claim 1, wherein the light source includes an incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, or combinations thereof.

8. The endoscope of claim 1, wherein the first camera chip includes silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations thereof.

9. A method of generating a fused image using an endoscope system, the method comprising:
providing the endoscope system of claim 1;
generating a first image from the first plurality of modulated photons;
generating a second image from the second plurality of modulated photons; and
overlaying the first image and the second image to thereby generate a fused image.

10. The method of claim 9, further comprising:
generating a third image from a third plurality of unmodulated photons.

11. The method of claim 10, wherein the third plurality of unmodulated photons are NIR photons, SWIR photons, eSWIR photons, or combinations thereof.

12. The method of claim 9, wherein the first plurality of modulated photons and the second plurality of modulated photons are VIS or VIS-NIR.

13. The endoscope system of claim 1, wherein the first plurality of source illumination fibers and the second plurality of source illumination fibers are arranged around the first camera chip at the distal end.

14. The endoscope system of claim 1, wherein the first plurality of source illumination fibers and the second plurality of source illumination fibers are arranged concentrically with respect to the first camera chip at the distal end.

* * * * *